(12) United States Patent
Ohnishi et al.

(10) Patent No.: US 7,714,480 B2
(45) Date of Patent: May 11, 2010

(54) PIEZOELECTRIC/ELECTROSTRICTIVE MEMBRANE SENSOR

(75) Inventors: Takao Ohnishi, Kiyosu (JP); Hideki Shimizu, Ohbu (JP); Takaaki Koizumi, Tajimi (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 12/316,745

(22) Filed: Dec. 16, 2008

(65) Prior Publication Data

US 2009/0102321 A1  Apr. 23, 2009

Related U.S. Application Data

(63) Continuation of application No. PCT/JP2007/063766, filed on Jul. 4, 2007.

(30) Foreign Application Priority Data

| Jul. 4, 2006 | (JP) | ............................ 2006-184061 |
| Aug. 14, 2006 | (JP) | ............................ 2006-221129 |
| Oct. 31, 2006 | (JP) | ............................ 2006-295870 |
| Mar. 14, 2007 | (JP) | ............................ 2007-065922 |

(51) Int. Cl.
*H01L 41/047* (2006.01)
*H01L 41/08* (2006.01)

(52) U.S. Cl. ........................ 310/324; 310/363; 310/358

(58) Field of Classification Search ................. 310/320, 310/324, 358, 363–366
See application file for complete search history.

(56) References Cited

U.S. PATENT DOCUMENTS

| 5,281,888 | A | 1/1994 | Takeuchi et al. |
| 5,376,857 | A | 12/1994 | Takeuchi et al. |
| 5,889,351 | A | 3/1999 | Okumura et al. |
| 6,531,070 | B1 | 3/2003 | Yamaguchi et al. |
| 7,276,994 | B2 * | 10/2007 | Takeuchi et al. ............ 333/189 |
| 2002/0158224 | A1 * | 10/2002 | Aoto et al. ................ 252/62.63 |
| 2003/0151331 | A1 * | 8/2003 | Akimune et al. ............. 310/358 |
| 2004/0231581 | A1 * | 11/2004 | Aoto et al. ...................... 117/2 |
| 2007/0220724 | A1 * | 9/2007 | Ohnishi et al. ............. 29/25.35 |
| 2008/0111452 | A1 * | 5/2008 | Koizumi et al. ............. 310/324 |
| 2009/0095072 | A1 * | 4/2009 | Shimizu et al. ............. 73/32 A |

FOREIGN PATENT DOCUMENTS

| JP | 02-051023 | A1 | 2/1990 |
| JP | 05-267742 | A1 | 10/1993 |
| JP | 06-260694 | A1 | 9/1994 |
| JP | 08-098884 | A1 | 4/1996 |
| JP | 08-201265 | A1 | 8/1996 |
| JP | 2001-146468 | A1 | 5/2001 |
| JP | 2001261435 | A | * | 9/2001 |
| JP | 2002261347 | A | * | 9/2002 |

(Continued)

*Primary Examiner*—J. SanMartin
(74) *Attorney, Agent, or Firm*—Burr & Brown (57) ABSTRACT

A piezoelectric/electrostrictive membrane sensor is provided, wherein a piezoelectric/electrostrictive body contains an alkali metal or an alkaline earth metal, and a sulfide and the main component of terminal electrodes are contained near the surface of the piezoelectric/electrostrictive body. A voltage equal to or higher than a withstand voltage is hardly applied to the piezoelectric/electrostrictive body, and consequently, the sensor is prevented from dielectric breakdown. In addition, the sensor is hardly electrostatically charged, and thus prevented from electrostatic discharge damage and attraction of dust, dirt or the like.

8 Claims, 6 Drawing Sheets
(3 of 6 Drawing Sheet(s) Filed in Color)

FOREIGN PATENT DOCUMENTS

| | | | |
|---|---|---|---|
| JP | 2004018321 A * | 1/2004 | |
| JP | 2004-186436 A1 | 7/2004 | |
| JP | 2005-014447 A1 | 1/2005 | |
| JP | 2005-164495 A1 | 6/2005 | |
| JP | 2005-191046 A1 | 7/2005 | |
| JP | 2006-128357 A1 | 5/2006 | |
| JP | 2007238376 A * | 9/2007 | |

* cited by examiner

PIEZOELECTRIC/ELECTROSTRICTIVE MEMBRANE SENSOR

TECHNICAL FIELD

The present invention relates to a piezoelectric/electrostrictive membrane sensor in which dielectric breakdown and electrostatic discharge damage are prevented.

BACKGROUND ART

A piezoelectric/electrostrictive membrane sensor can be used for measuring fluid characteristics such as viscosity, density and concentration by use of the mechano-electric transduction of a piezoelectric/electrostrictive element in which a membranous piezoelectric/electrostrictive body disposed in the sensor is sandwiched between a pair of electrodes. When the piezoelectric/electrostrictive membrane sensor (the piezoelectric/electrostrictive element) oscillates in a fluid, the sensor receives a mechanical resistance due to the viscosity resistance of the fluid, and the electric constant of the piezoelectric/electrostrictive element changes in a constant relation with respect to the mechanical resistance. Therefore, the sensor can detect the electric constant to measure the viscosity of the fluid or the like.

It is to be noted that any prior document having the same theme as or a theme in common with the theme of the present invention discussed later does not seem to be present, however, Patent Documents 1 to 6 can be given as examples of a prior document for reference of the piezoelectric/electrostrictive membrane sensor:

Patent Document 1: JP-A-8-201265
Patent Document 2: JP-A-5-267742
Patent Document 3: JP-A-6-260694
Patent Document 4: JP-A-2005-164495
Patent Document 5: JP-A-2-51023
Patent Document 6: JP-A-8-98884

In recent years, the above piezoelectric/electrostrictive membrane sensor (hereinafter referred simply as the sensor) has the following problems in the same manner as in a semiconductor integrated circuit chip (IC, LSI) or the like.

First, there are such problems that a membranous piezoelectric/electrostrictive body (an insulator) causes dielectric breakdown and that the piezoelectric/electrostrictive membrane sensor cannot operate. In a chip made of silicon, there is a known problem that to speed up the operation, it is essential to form a thin membrane and apply a high voltage (electric field), and hence an oxide membrane (the insulator) easily causes the dielectric breakdown. Similarly, in the piezoelectric/electrostrictive membrane sensor, sometimes the applied voltage is made high by thinning the membrane of the piezoelectric/electrostrictive body, for example, in case of a longitudinally effective oscillating element. This is because the oscillation becomes larger when the applied voltage to the piezoelectric/electrostrictive body made of a thin membrane is increased; thereby the sensitivity of the sensor is effectively increased. However, in this case, the piezoelectric/electrostrictive body easily causes the dielectric breakdown. Consequently, the deterioration of the reliability of the piezoelectric/electrostrictive membrane sensor is incurred. Therefore, the prevention of the dielectric breakdown in this case still remains a theme to be solved.

Moreover, in association with the above dielectric breakdown, breakdown due to static electricity (electrostatic discharge damage) has raised a problem. All matter has electrons in atoms. When articles constituted of such matter, or a person and the article come in contact with (including friction, collision, etc.) or peel from each other, the electrons move, and an electrically unstable state is supposedly brought to generate the static electricity. When the static electricity is generated, with the movement of the electrons, the article or the person receiving the electrons forms a minus pole, and the article or the person discharging the electrons forms a plus pole. In the case of the piezoelectric/electrostrictive membrane sensor, the piezoelectric/electrostrictive body as an insulator receives the electrons from another article, the person or air on the surface of the body, and can be brought into a charged state with the minus pole. Moreover, when the body discharges the electrons (discharges electricity) to the other article, the person or the air from this state, a voltage of several kVs is applied during the discharge, and the piezoelectric/electrostrictive body is sometimes damaged (the electrostatic discharge damage). Furthermore, when dust, dirt or the like charged with the plus pole is attracted to adhere to the surface of the piezoelectric/electrostrictive body in the charged state with the minus pole, a pair of electrodes sandwiching the piezoelectric/electrostrictive body therebetween thus causes short circuit, any desired voltage is not applied to the piezoelectric/electrostrictive body, the oscillation of the sensor becomes unstable. Alternatively, the resonance frequency of the sensor deviates owing to the mass of the dust or the like to cause wrong detection or the like. The characteristics of a fluid or the presence of the fluid can not correctly be measured.

SUMMARY OF THE INVENTION

The present invention has been developed in view of such a situation, and an object thereof is to provide a piezoelectric/electrostrictive membrane sensor in which a voltage equal to or higher than a withstand voltage is hardly applied to a piezoelectric/electrostrictive body. Consequently, the sensor is prevented from dielectric breakdown, is hardly electrostatically charged, and thus prevented from electrostatic discharge damage and attraction of dust, dirt or the like. As a result of investigations, it has been found that the above object can be achieved by the piezoelectric/electrostrictive membrane sensor in which a sulfide and the main components of terminal electrodes are appropriate present near the surface of a piezoelectric/electrostrictive body.

That is, according to the present invention, there is provided a piezoelectric/electrostrictive membrane sensor comprising: a ceramic substrate having a thin diaphragm portion and a thick portion integrally provided on the peripheral edge of the thin diaphragm portion, and including a cavity formed by the thin diaphragm portion and the thick portion so as to communicate with the outside; a piezoelectric/electrostrictive element having a laminate structure arranged on the outer surface of the thin diaphragm portion of the ceramic substrate and including a membranous piezoelectric/electrostrictive body, and a lower electrode and an upper electrode between which the piezoelectric/electrostrictive body is sandwiched; and terminal electrodes which connect the lower electrode and the upper electrode to a power source, the thin diaphragm portion of the ceramic substrate being configured to oscillate in conjunction with the driving of the piezoelectric/electrostrictive element, wherein the piezoelectric/electrostrictive body contains an alkali metal or an alkaline earth metal, and a sulfide and a main component of the terminal electrodes is contained near the surface of the piezoelectric/electrostrictive body.

In the piezoelectric/electrostrictive membrane sensor according to the present invention, an auxiliary electrode may be provided so as to connect the terminal electrode (for the upper electrode) arranged on the ceramic substrate to the upper electrode formed on the piezoelectric/electrostrictive body. When the auxiliary electrode is provided, the electrode can be formed of the same material as that of the upper electrode. Alternatively, the auxiliary electrode may be constituted as a part of the upper electrode. The lower electrode is arranged on the ceramic substrate, and is hence directly connected to the terminal electrode (for the lower electrode) similarly arranged on the ceramic substrate, and the auxiliary electrode is not necessary between the lower electrode and the terminal electrode (for the lower electrode). It is to be noted that in the present description, the vicinity of the surface of the piezoelectric/electrostrictive body is not the vicinity of the surface only, includes the surface and the vicinity of the surface, and indicates a portion near the surface, the portion including the surface.

In the piezoelectric/electrostrictive membrane sensor according to the present invention, the sulfide contained near the surface of the piezoelectric/electrostrictive body is formed at a time when the alkali metal or the alkaline earth metal contained in the piezoelectric/electrostrictive body bonds with sulfur (near the surface of the piezoelectric/electrostrictive body) by a heat treatment.

In other words, to manufacture the piezoelectric/electrostrictive membrane sensor, the heat treatment (e.g., a firing treatment) is performed, the alkali metal or the alkaline earth metal contained in the piezoelectric/electrostrictive body is allowed to react with sulfur in air, and the sulfide can be generated near the surface of the piezoelectric/electrostrictive body to obtain the sensor. The air should always contain sulfur, unless in an extraordinary clean room, however, the amount of sulfur is quite small, though. Therefore, a remarkably, but quite small amount of the sulfide is contained near the surface of the piezoelectric/electrostrictive body.

Moreover, sulfur can beforehand be contained in the material of the electrodes to form the sulfide. This is preferable means for obtaining the piezoelectric/electrostrictive membrane sensor according to the present invention. This is because it is possible to minimize extremely an amount of the sulfide contained near the surface of the piezoelectric/electrostrictive body by adjusting the amount to be contained in materials for the electrodes.

In the piezoelectric/electrostrictive membrane sensor according to the present invention, the main component of the terminal electrodes contained near the surface of the piezoelectric/electrostrictive body is preferably one formed as a result of diffusion from the terminal electrodes to the vicinity of the surface of the piezoelectric/electrostrictive body by a heat treatment after the forming of the terminal electrodes.

In other words, the piezoelectric/electrostrictive membrane sensor according to the present invention can be obtained by forming the terminal electrodes, and then performing the heat treatment (the firing treatment) to diffuse (thermally diffuse) the main component of the conductive material constituting the terminal electrodes to near the surface of the piezoelectric/electrostrictive body. Therefore, an extremely smaller amount of the main component of the terminal electrodes is contained near the surface of the piezoelectric/electrostrictive body.

In the piezoelectric/electrostrictive membrane sensor according to the present invention, the terminal electrodes are preferably constituted of silver or a conductive material containing this metal as the main component.

In the piezoelectric/electrostrictive membrane sensor according to the present invention, the upper electrode is preferably constituted of gold or a conductive material containing this metal as the main component.

In the piezoelectric/electrostrictive membrane sensor according to the present invention, the lower electrode is preferably constituted of platinum or a conductive material containing this metal as the main component. It is to be noted that the electrode simply mentioned in the present description indicates all of the terminal electrodes, the upper electrode, the lower electrode, and the auxiliary electrode (if any).

In the piezoelectric/electrostrictive membrane sensor according to the present invention, the piezoelectric/electrostrictive body is preferably constituted of $(Bi_{0.5}Na_{0.5})TiO_3$ or a piezoelectric/electrostrictive material containing this metal as the main component. That is, preferable examples of the alkali metal or the alkali earth metal contained in the piezoelectric/electrostrictive body include sodium.

The piezoelectric/electrostrictive membrane sensor according to the present invention comprises the piezoelectric/electrostrictive element arranged on the thin diaphragm portion, and the thin diaphragm portion oscillates in conjunction with the driving of the piezoelectric/electrostrictive element, so that the sensor can be used as a heretofore known sensor for measuring fluid characteristics such as viscosity, density and concentration (see Patent Documents 1 to 4). With vibrating the piezoelectric/electrostrictive membrane sensor (the piezoelectric/electrostrictive element) in a fluid, the viscosity of the fluid can be measured by detecting the changes in the electric constant of the piezoelectric/electrostrictive element in a constant relation with respect to the mechanical resistance caused by the viscosity resistance of the fluid, which is given to the sensor.

In addition, the piezoelectric/electrostrictive membrane sensor according to the present invention is high in the reliability since the piezoelectric/electrostrictive body contains the sulfide near its surface, and the piezoelectric/electrostrictive body is hardly exposed to a voltage equal to or higher than a withstand voltage, thereby the present sensor is prevented from dielectric breakdown. The sulfide shows conductivity at a certain level of humidity, and hence a portion containing the sulfide near the surface of the piezoelectric/electrostrictive body lowers insulation resistance between the upper electrode and the lower electrode on both sides of the piezoelectric/electrostrictive body as an insulator. Therefore, even in case of the use under the conditions where a high voltage is applied, even when an abnormally high voltage is applied due to any cause, electricity is conducted through the portion where the insulation resistance is lowered (a short circuit current slightly flows); thus, the discharge between the electrodes is resultantly prevented. Therefore, in the piezoelectric/electrostrictive membrane sensor according to the present invention, the voltage applied to the piezoelectric/electrostrictive body is not easily in excess of the withstand voltage. Moreover, the dielectric breakdown on the surface of the membranous piezoelectric/electrostrictive body is generated before the dielectric breakdown of the membranous piezoelectric/electrostrictive body in a thickness direction. In consequence, the fatal breakdown of the membranous piezoelectric/electrostrictive body in the thickness direction can be prevented, thereby preventing the dielectric breakdown.

In the piezoelectric/electrostrictive membrane sensor according to the present invention, when an ambient humidity increases, a current can be allowed to leak at the surface of the piezoelectric/electrostrictive body to prevent a water content from permeating the piezoelectric/electrostrictive body and causing the breakdown. Therefore, even with the fluctuations of the humidity during seasons, the breakdown would not easily occur.

In the heretofore known piezoelectric/electrostrictive membrane sensor, no sulfide is contained near the surface of the piezoelectric/electrostrictive body. Moreover, heretofore, no technology for containing the sulfide near the surface of the piezoelectric/electrostrictive body in the piezoelectric/electrostrictive membrane sensor has been known. Therefore, in the conventional piezoelectric/electrostrictive membrane sensor, the problem of dielectric breakdown might occur in the same manner as in a chip made of silicon or the like. However, according to the piezoelectric/electrostrictive membrane sensor of the present invention, such a problem can be avoided.

According to the piezoelectric/electrostrictive membrane sensor of the present invention, the dielectric breakdown of the membranous piezoelectric/electrostrictive body is prevented. Therefore, as compared with the conventional piezoelectric/electrostrictive membrane sensor, a thinner piezoelectric/electrostrictive body can be provided, and a higher voltage can be applied. Consequently, as compared with the conventional piezoelectric/electrostrictive membrane sensor, the sensor can oscillate with larger amplitude, and the sensitivity of the sensor is improved.

In the preferable embodiment of the piezoelectric/electrostrictive membrane sensor according to the present invention, the sulfide contained near the surface of the piezoelectric/electrostrictive body is formed at a time when the alkali metal or the alkaline earth metal contained in the piezoelectric/electrostrictive body bonds with sulfur in the air or sulfur contained in the material of the electrodes (near the surface of the piezoelectric/electrostrictive body) by the heat treatment. Accordingly, a noticeably small amount of the sulfide is contained near the surface of the piezoelectric/electrostrictive body. Thus, the voltage equal to or higher than the withstand voltage is hardly applied to the piezoelectric/electrostrictive body. However, since the short circuit current noticeably slightly flows between the upper electrode and the lower electrode, a desired voltage is applied to the piezoelectric/electrostrictive body. Therefore, the piezoelectric/electrostrictive element can be driven, the thin diaphragm portion can oscillate in conjunction with the driving of the element, and the sensor can show an excellent performance.

In the preferable embodiment of the piezoelectric/electrostrictive membrane sensor according to the present invention, at least one of gold and platinum is contained in the material of the electrodes. Therefore, in a case where the sulfide contained near the surface of the piezoelectric/electrostrictive body is constituted at a time when the alkali metal or the alkaline earth metal contained in the piezoelectric/electrostrictive body bonds with sulfur included in the air or the material of the electrodes (and remaining even after firing), at least one of gold and platinum serves as a catalyst to promote the bonding reaction. Consequently, in this case, the noticeably small amount of the sulfide is surely contained near the surface of the piezoelectric/electrostrictive body.

In addition, the piezoelectric/electrostrictive membrane sensor according to the present invention contains the main component of the terminal electrodes near the surface of the piezoelectric/electrostrictive body, and is hardly electrostatically charged, so that the sensor is prevented from electrostatic discharge damage, and has a high reliability even in this respect. Since the main component of the terminal electrodes is the conductive material, a portion containing the main component of the terminal electrodes near the surface of the piezoelectric/electrostrictive body is a low resistance portion. Even when the surface of the piezoelectric/electrostrictive body as an insulator receives electrons, the electrons are immediately discharged through a lower resistance portion. Therefore, the piezoelectric/electrostrictive membrane sensor according to the present invention is not easily brought into a state in which the sensor is electrostatically charged with the accumulated electrons. Consequently, in addition to the prevention of the electrostatic discharge damage, any dust, dirt or the like is not attracted or does not adhere to the surface. There is not easily generated any problem due to the attraction, for example, a problem that the lowering of the precision of the sensor in a case where the upper electrode and the lower electrode sandwiching the piezoelectric/electrostrictive body therebetween causes short circuit and that any desired voltage cannot be applied to the piezoelectric/electrostrictive body.

According to the piezoelectric/electrostrictive membrane sensor of the present invention, even in a state in which the sulfide is locally not present near the surface, the above fatal dielectric breakdown can be prevented. That is, even when dew condensation (including micro dew on the surface of the piezoelectric/electrostrictive body) occurs with a high humidity and the sulfide locally gathers, any electron on the surface does not move. Therefore, the performance of the piezoelectric/electrostrictive membrane sensor is obtained in a stable state.

As the heretofore known piezoelectric/electrostrictive membrane sensor, the sensor is not present in which the main component of the terminal electrodes is contained near the surface of the piezoelectric/electrostrictive body. Moreover, heretofore in the piezoelectric/electrostrictive membrane sensor, a technology has not been known in which the main component of the terminal electrodes is contained near the surface of the piezoelectric/electrostrictive body. Therefore, in the conventional piezoelectric/electrostrictive membrane sensor, the problem of the electrostatic discharge damage might constantly occurs in the same manner as in another electronic component including a semiconductor integrated circuit chip, but according to the piezoelectric/electrostrictive membrane sensor of the present invention, such a problem can be avoided.

In the preferable embodiment of the piezoelectric/electrostrictive membrane sensor according to the present invention, the main component of the terminal electrodes contained near the surface of the piezoelectric/electrostrictive body is diffused from the terminal electrodes to the vicinity of the surface of the piezoelectric/electrostrictive body by the heat treatment after the forming of the terminal electrodes. Therefore, the remarkably small amount of the main component of the terminal electrodes is contained near the surface of the piezoelectric/electrostrictive body. Consequently, the sensor is hardly electrostatically charged. On the other hand, the main component of the terminal electrodes contained near the surface of the piezoelectric/electrostrictive body does not cause the short circuit between the upper electrode and the lower electrode, and the desired voltage can be applied to the piezoelectric/electrostrictive body. In consequence, the piezoelectric/electrostrictive element can be driven to oscillate the thin diaphragm portion in conjunction with the driving of the element, and the sensor can exert the excellent performance.

In the preferable embodiment of the piezoelectric/electrostrictive membrane sensor according to the present invention, the terminal electrodes are constituted of silver as a low melting point material or the conductive material containing this metal as the main component. The auxiliary electrode and the upper electrode are constituted of gold having a melting point higher than that of silver, or the conductive material containing this metal as the main component. Therefore, only silver as the main component of the terminal electrodes is easily contained near the surface of the piezoelectric/electrostrictive body by diffusion accompanying the heat treatment.

That is, it can be said that the preferable embodiment of the piezoelectric/electrostrictive membrane sensor according to the present invention is easily manufactured.

In the preferable embodiment of the piezoelectric/electrostrictive membrane sensor according to the present invention, the piezoelectric/electrostrictive body is constituted of $(Bi_{0.5}Na_{0.5})TiO_3$ having large residual polarization or the piezoelectric/electrostrictive material containing this metal as the main component, so that the sensor can realize a high output.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF REFERENCE NUMERALS USED IN THE DRAWINGS

1: ceramic substrate;
2: thick portion
3: thin diaphragm portion;
4: lower electrode;
5: piezoelectric/electrostrictive body;
6: upper electrode;
7: joining layer;
8: auxiliary electrode;
9: through hole;
10; cavity;
12: piezoelectric/electrostrictive element;
18; terminal electrode;
19; terminal electrode;
20: piezoelectric/electrostrictive membrane sensor.

DETAILED DESCRIPTION OF THE INVENTION

Embodiments of the present invention will hereinafter be described appropriately with reference to the drawings, but the present invention is not limited to these embodiments, when interpreted. The present invention can variously be changed, modified, improved and replaced based on the knowledge of a person skilled in the art without departing from the scope of the present invention. For example, the drawings show the preferable embodiments of the present invention, but the present invention is not restricted by embodiment or information shown in the drawings. To implement or verify the present invention, means similar or equivalent to means described in the present description is applicable, but preferable means is the following means.

Figure 1:
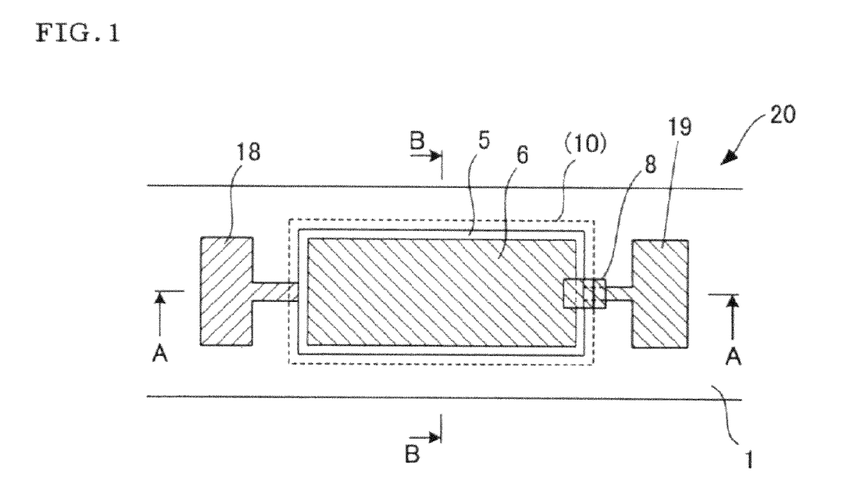
FIG. 1 is a plan view showing one embodiment of a piezoelectric/electrostrictive membrane sensor according to the present invention.

First, the constitution of a piezoelectric/electrostrictive membrane sensor according to the present invention will be described. FIG. 1 is a plan view (a top view) showing one embodiment of the piezoelectric/electrostrictive membrane sensor according to the present invention, FIG. 2 is a sectional view showing a section cut along the line AA in FIG. 1, and FIG. 3 is a sectional view showing a section cut along the line BB in FIG. 1.

Figure 2:
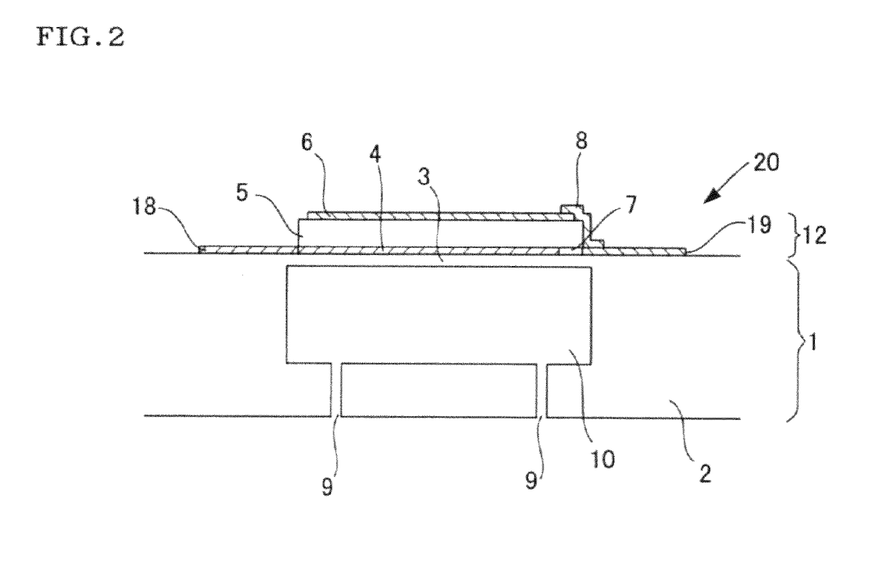
FIG. 2 is a sectional view showing a section cut along the line AA in FIG. 1.
Figure 3:
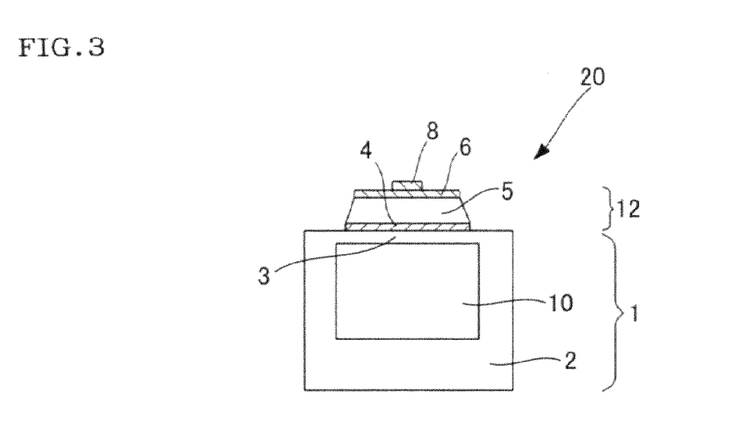
FIG. 3 is a sectional view showing a section cut along the line BB in FIG. 1.

A piezoelectric/electrostrictive membrane sensor 20 shown in FIGS. 1 to 3 includes a ceramic substrate 1 and a piezoelectric/electrostrictive element 12. The ceramic substrate 1 has a thin diaphragm portion 3 and a thick portion 2 integrally provided on the peripheral edge of the thin diaphragm portion 3, and the ceramic substrate 1 is provided with a cavity 10 formed by the thin diaphragm portion 3 and the thick portion 2 so as to communicate with the outside via through holes 9. The piezoelectric/electrostrictive element 12 is arranged on the outer surface of the thin diaphragm portion 3 of the ceramic substrate 1, and has a laminate structure formed by a membranous piezoelectric/electrostrictive body 5 and a pair of membranous electrodes (an upper electrode 6 and a lower electrode 4) sandwiching the piezoelectric/electrostrictive body 5 therebetween.

In the piezoelectric/electrostrictive membrane sensor 20, the lower electrode 4 formed on the thin diaphragm portion 3 of the ceramic substrate 1 on the underside of the piezoelectric/electrostrictive body 5 is directly and conductively connected to a terminal electrode 18 (for the lower electrode). The upper electrode 6 formed on the upside of the piezoelectric/electrostrictive body 5 is conductively connected to a terminal electrode 19 (for the upper electrode) via an auxiliary electrode 8. It is to be noted that the auxiliary electrode 8 inherently constitutes a part of the upper electrode 6, but in the present embodiment (the piezoelectric/electrostrictive membrane sensor 20), to facilitate the understanding of a function, the auxiliary electrode 8 is shown.

The terminal electrode 19 (for the upper electrode) is insulated from the lower electrode 4 by a joining layer 7 sandwiched between the electrodes. The joining layer 7 is formed so as to be penetrated into the underside of the piezoelectric/electrostrictive body 5, and is a layer having a function of connecting the piezoelectric/electrostrictive body 5 to the thin diaphragm portion 3. The piezoelectric/electrostrictive body 5 is formed in such a size as to cover the lower electrode 4, and the upper electrode 6 is formed so as to straddle the piezoelectric/electrostrictive body 5. A sulfide and a main component of the terminal electrodes 18, 19 described later are contained in a location near the exposed surface of the piezoelectric/electrostrictive body 5, which is not covered with the upper electrode 6 and the auxiliary electrode 8. It is to be noted that the joining layer 7 is appropriately applicable in accordance with the application of the sensor, and a joining layer 7 portion may be brought into an incompletely joined state.

In the piezoelectric/electrostrictive membrane sensor 20, when the piezoelectric/electrostrictive element 12 is driven (displacement is generated), the thin diaphragm portion 3 of the ceramic substrate 1 oscillates in conjunction with the driving. The thin diaphragm portion 3 of the ceramic substrate 1 usually has a thickness of 50 μm or less, preferably 30 μm or less, further preferably 15 μm or less so that the oscillation of the piezoelectric/electrostrictive body 5 is not disturbed. As the planar shape of the thin diaphragm portion 3, any shape such as a rectangular shape, a square shape, a triangular shape, an elliptic shape or a perfectly circular shape may be employed, but the rectangular shape or the perfectly circular shape is selected if necessary, in the application of the sensor in which a resonance mode to be excited needs to be simplified.

Next, the material of each constitutional requirement of the piezoelectric/electrostrictive membrane sensor according to the present invention will be described in accordance with the piezoelectric/electrostrictive membrane sensor 20 as an example.

The material for use in the ceramic substrate 1 is preferably a material having thermal resistance, chemical stability and insulation properties. This is because the lower electrode 4, piezoelectric/electrostrictive body 5 and the upper electrode 6 are sometimes thermally treated when integrated. Moreover, when the piezoelectric/electrostrictive membrane sensor 20 detects the characteristics of a solution, the solution sometimes has conductivity or corrosive properties. Examples of a preferably usable material include stabilized zirconium oxide, partially stabilized zirconium oxide, aluminum oxide, magnesium oxide, mullite, aluminum nitride, silicon nitride and glass. Among these materials, stabilized zirconium oxide and partially stabilized zirconium oxide are most preferable, because the materials keep a high mechanical strength or have an excellent tenacity or the like even in a case where the thin diaphragm portion 3 is remarkably thinly formed.

As the material of the piezoelectric/electrostrictive body 5, any material may be used as long as the material contains an alkali metal or an alkaline earth metal and exerts a piezoelectric/electrostrictive effect. Examples of a preferable material satisfying the conditions include $(Bi_{0.5}Na_{0.5})TiO_3$ or a material containing this metal as the main component, or $(1-x)(Bi_{0.5}Na_{0.5})TiO_3$-$xKNbO_3$ (x is a molar fraction of $0 \leq x \leq 0.06$) or a material containing this metal as the main component.

As the material of the joining layer 7, an organic or inorganic material having close contact properties and joining properties with respect to both the piezoelectric/electrostrictive body 5 and the ceramic substrate 1 may be used. The material for use preferably has a thermal expansion coefficient having an intermediate value between the thermal expansion coefficient of the material of the ceramic substrate 1 and the thermal expansion coefficient of the material for use in the piezoelectric/electrostrictive body 5 in order to obtain highly reliable joining properties. When the piezoelectric/electrostrictive body 5 is thermally treated, a glass material having a softening point higher than the heat treatment temperature of the piezoelectric/electrostrictive body 5 is preferably used. The piezoelectric/electrostrictive body 5 is firmly joined to the ceramic substrate 1, and deformation by the heat treatment is suppressed owing to the high softening point. Furthermore, when the piezoelectric/electrostrictive body 5 is constituted of one of the above two preferable materials, as the material of the joining layer 7, a material containing $(1-x)(Bi_{0.5}Na_{0.5})TiO_3$-$xKNbO_3$ (x is a molar fraction of $0.08 \leq x \leq 0.5$) as the main component is preferably employed. This is because the material has high close contact properties with respect to both the piezoelectric/electrostrictive body 5 and the ceramic substrate 1, and the piezoelectric/electrostrictive body 5 and the ceramic substrate 1 can be prevented from being adversely affected during the heat treatment. That is, since the material has a component similar to that of the piezoelectric/electrostrictive body 5, the material has high close contact properties with respect to the piezoelectric/electrostrictive body 5. Moreover, there are fewer problems due to the diffusion of a heterologous element, which might be generated in a case where glass is used. Furthermore, since much $KNbO_3$ is contained, the material has a high reactivity with the ceramic substrate 1, and firm joining is possible. In addition, $(1-x)(Bi_{0.5}Na_{0.5})TiO_3$-$xKNbO_3$ (x is the molar fraction of $0.08 \leq x \leq 0.5$) hardly exerts piezoelectric/electrostrictive characteristics. Therefore, during use, any displacement is not generated with respect to an electric field generated in the lower electrode 4 and the auxiliary electrode 8, and hence stable sensor characteristics can be obtained.

As to the materials of the electrodes, the terminal electrodes employ silver or a conductive material containing this metal as the main component, the auxiliary electrode and the upper electrode employ gold or a conductive material containing this metal as the main component, and the lower electrode employs platinum or a conductive material containing this metal as the main component.

Next, a manufacturing method of the piezoelectric/electrostrictive membrane sensor according to the present invention will be described in accordance with the manufacturing of the piezoelectric/electrostrictive membrane sensor 20 as an example.

(Step 1. Preparation of Ceramic Substrate) The ceramic substrate 1 can be prepared by a green sheet laminating process. Specifically, the predetermined numbers of ceramic green sheets constituted of the above-mentioned ceramic material as the main component are prepared. A hole portion having a predetermined shape constituting the cavity 10 after the lamination is made in the necessary number of the resultant ceramic green sheets by use of a punch processor including a punch and a die, and hole portions having a predetermined shape forming the through holes 9 after the lamination are made in the necessary number of the other sheets. Then, the ceramic green sheet constituting the thin diaphragm portion 3 later, the ceramic green sheet having the hole portion made so as to constitute the cavity 10, and the ceramic green sheet having the hole portion made so as to constitute the through holes 9 are laminated in this order to obtain a laminated green article, and the article is fired to obtain the ceramic substrate 1. One ceramic green sheet has a thickness of about 100 to 300 μm excluding the ceramic green sheet constituting the thin diaphragm portion 3.

The ceramic green sheet can be prepared by a heretofore known ceramic manufacturing method. One example will be described. Desired ceramic material powder is prepared, and blended with a binder, a solvent, a dispersant, a plasticizer or the like in a desired composition to prepare a slurry, and this slurry is subjected to a defoaming treatment and a sheet forming process such as a doctor blade process, a reverse roll coater process or a reverse doctor roll coater process, whereby the ceramic green sheet can be obtained.

(Step 2. Formation of Lower Electrode) After forming a membrane by any known membrane forming technique, the formed membrane is dried and fired to form the membranous lower electrode 4 on the outer surface of the thin diaphragm portion 3 of the ceramic substrate 1. Specifically, as the membrane forming technique, a thin membrane forming technique such as ion beam, sputtering, vacuum deposition, CVD, ion plating or plating or a thick membrane forming technique such as screen printing, spray or dipping is appropriately selected. In particular, the sputtering process or the screen printing process is preferably selected. The membrane is dried at 50 to 150° C., and fired at 1100 to 1300° C. Firing time is about one to two hours.

(Step 3. Formation of Joining Layer) To form the joining layer 7, a usual thick membrane technique is used. In particular, a stamping process or the screen printing process is preferably used. Moreover, when a portion to be formed has a size of about several ten µms to several hundred µms, an ink jet process is preferably used. When the joining layer 7 needs to be thermally treated, the layer may thermally be treated before forming the next piezoelectric/electrostrictive body 5, after forming the piezoelectric/electrostrictive body 5 or simultaneously with the forming.

(Step 4. Formation of Piezoelectric/Electrostrictive Body) To form the membranous piezoelectric/electrostrictive body 5, a membrane is formed by a known any membrane forming process, and fired in the same manner as in the lower electrode 4. From a viewpoint of cost reduction, as a membrane forming technique, the screen printing is preferably used. The membrane has a thickness of preferably 100 µm or less, further preferably 50 µm or less for increasing displacement (i.e., improving characteristics), more preferably 5 to 20 µm. The thus formed piezoelectric/electrostrictive body 5 is integrated with the beforehand formed lower electrode 4 and joining layer 7 during the firing. Firing temperature is in a range of about 900 to 1400° C., and firing time is in a range of about two to 50 hours. The membrane is preferably fired while controlling the atmosphere together with an evaporation source of the piezoelectric/electrostrictive material so that the piezoelectric/electrostrictive body 5 does not become unstable at a high temperature.

(Step 5. Formation of Terminal Electrodes) To form the terminal electrode 19 for the upper electrode 6 and the terminal electrode 18 for the lower electrode 4, membranes are formed by a membrane forming process similar to that of the lower electrode 4, dried and fired. During the firing, the terminal electrode 18 is joined to the lower electrode 4 and the piezoelectric/electrostrictive body 5 to form an integral structure.

(Step 6. Formation of Upper Electrode) To form the upper electrode 6, a membrane is formed by a membrane forming process similar to that of the lower electrode 4, dried and fired. The membrane is fired at 500 to 900° C., and firing time is in a range of about one to two hours.

In this step of forming the upper electrode, the main component (silver) of the beforehand formed terminal electrodes 18, 19 is thermally diffused, and contained near the surface of the beforehand formed piezoelectric/electrostrictive body 5.

Figure 4:
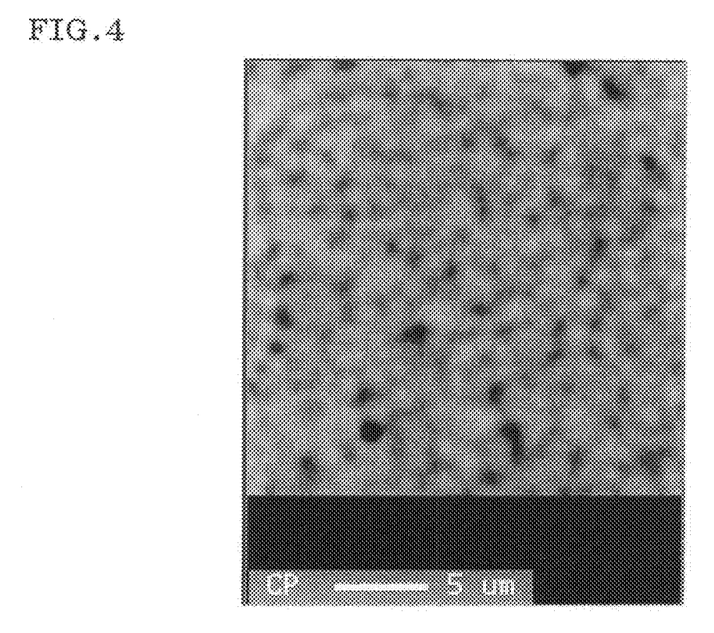
FIG. 4 is a diagram showing one embodiment of the piezoelectric/electrostrictive membrane sensor according to the present invention, and is a photograph showing the surface of a piezoelectric/electrostrictive body by a scanning electron microscope.
Figure 5:
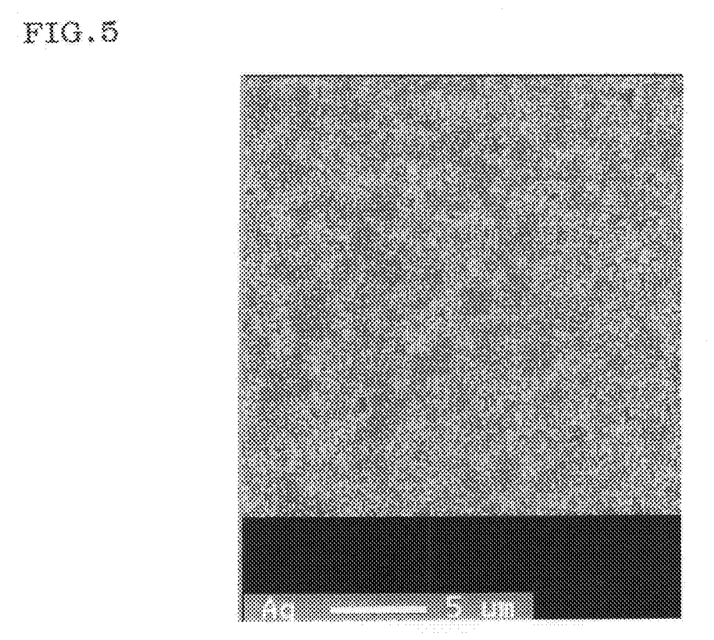
FIG. 5 is a diagram showing one embodiment of the piezoelectric/electrostrictive membrane sensor according to the present invention, and is a photograph showing the surface of the piezoelectric/electrostrictive body by an X-ray micro analyzer (EPMA, Electron Probe Micro Analyzer) and showing a behavior that silver as the material of terminal electrodes is diffused in the piezoelectric/electrostrictive body.

FIGS. 4 and 5 are diagrams showing one embodiment of the piezoelectric/electrostrictive membrane sensor according to the present invention. FIG. 4 is a photograph showing the surface of the piezoelectric/electrostrictive body by a scanning electron microscope. Moreover, FIG. 5 is a photograph showing the surface of the piezoelectric/electrostrictive body by an X-ray micro analyzer (EPMA, Electron Probe Micro Analyzer) and showing a behavior that silver as the material of the terminal electrode diffuses into the piezoelectric/electrostrictive body. It is to be noted that the photograph of the EPMA shows that a target matter gradually increases (is present) in order of blue, green, yellow, vermillion and red (blue shows the smallest amount, and red shows the largest amount). After forming (including firing) the terminal electrode, the upper electrode is formed (including the firing), so that as shown in FIG. 5, silver as the material of the terminal electrodes 18, 19 can be contained near the surface of the piezoelectric/electrostrictive body 5. Silver is preferably present in a pole surface layer in a thickness direction, and silver can be present near the surface of the piezoelectric/electrostrictive body 5 by sputtering or the like. However, silver is preferably thermally diffused in that silver can more thinly, easily and uniformly be diffused in the pole surface layer and in that resistance can slightly be lowered while keeping insulation. It is to be noted that in an example in which the membrane thickness of the piezoelectric/electrostrictive body 5 was set to 5 to 20 µm, it has been confirmed that silver was diffused in a state in which the membrane thickness was 2 µm or less and that satisfactory characteristics were obtained.

Moreover, the firing temperature can be adjusted or the content of the main component (silver) included in a material for use in forming the terminal electrodes 18, 19 can be adjusted to adjust the amount of the main component (silver) of the terminal electrodes 18, 19 contained near the surface of the piezoelectric/electrostrictive body 5 of the resultant piezoelectric/electrostrictive membrane sensor 20.

(Step 7. Formation of Auxiliary Electrode) To form the auxiliary electrode 8, a membrane is formed by a membrane forming process similar to that of the upper electrode 6, dried and fired. During the firing, the auxiliary electrode 8 is joined to the upper electrode 6, the piezoelectric/electrostrictive body 5 and the terminal electrode 19 to form an integral structure.

The piezoelectric/electrostrictive element 12 is obtained as described above, but the piezoelectric/electrostrictive element 12 only may be separately prepared, and attached to the ceramic substrate 1 or directly formed on the ceramic substrate 1.

It is to be noted that as long as the firing is performed in the step of forming the terminal electrodes 18, 19 and the firing is performed in the step of forming the upper electrode 6, to form the lower electrode 4, the joining layer 7, the piezoelectric/electrostrictive body 5 and the terminal electrodes 18, 19, instead of the firing (the heat treatment) of each formed membrane described above, the membranes may be successively formed and collectively and simultaneously fired (thermally treated). Similarly, to form the upper electrode 6 and the auxiliary electrode 8, instead of the firing (the heat treatment) of each formed membrane, the membranes may be successively formed and collectively and simultaneously fired (thermally treated). In this case, to realize satisfactory joining properties, needless to say, the temperature is appropriately selected.

In the above steps, the piezoelectric/electrostrictive membrane sensor 20 including the ceramic substrate 1 and the piezoelectric/electrostrictive element 12 is structurally completed.

(Step 8. Polarization) A direct-current high voltage (e.g., a voltage of DC 300 V) is applied across the upper electrode 6 and the lower electrode 4 in the piezoelectric/electrostrictive element 12 of the piezoelectric/electrostrictive membrane sensor 20 to perform a polarization treatment.

(Step 9. Displacement Measurement) An alternate-current sine wave voltage of 0 to 200 V, 1 kHz is applied, and the displacement of the piezoelectric/electrostrictive element 12 of the piezoelectric/electrostrictive membrane sensor 20 subjected to the polarization treatment is measured using a laser Doppler oscillation meter.

(Step 10. UV Sheet Attachment) A large number of piezoelectric/electrostrictive membrane sensors 20 are usually manufactured at once. In this case, a UV sheet is attached as fixing means to the surface of the piezoelectric/electrostrictive membrane sensor 20 on a side opposite to the piezoelectric/electrostrictive element 12, and fixed to a predetermined position.

(Step 11. Outer Shape Cutting) When a large number of sensors are formed, the prior steps are performed without performing cutting, but here the cutting is performed using a dicer to obtain the individual piezoelectric/electrostrictive membrane sensors 20.

(Step 12. Sorting) To select satisfactory articles, articles having a displacement of a reference value or less in Step 9 are deleted as defective articles.

(Step 13. Heat Treatment) The outer shape cutting is usually performed while performing washing with water. Therefore, to remove water, the acceptable articles are subjected to a heat treatment to dry. Temperature conditions are in a range of 60° C. or more and 900° C. or less. Even by temperature adjustment in this step, the amount of the main component (silver) of the terminal electrodes 18, 19 contained near the surface of the piezoelectric/electrostrictive body 5 of the resultant piezoelectric/electrostrictive membrane sensor 20 can be adjusted.

A plurality of heat treatments including this last heat treatment and the firing performed before the heat treatment allow the alkali metal or the alkaline earth metal contained in the piezoelectric/electrostrictive body 5 to react with sulfur in air and sulfur contained in the material of the electrodes and remaining after the firing, to form a sulfide near the surface of the piezoelectric/electrostrictive body, so that the sulfide is contained near the surface. When the piezoelectric/electrostrictive body 5 is $(Bi_{0.5}Na_{0.5})TiO_3$, the compound of sodium and sulfur is contained near the surface of the piezoelectric/electrostrictive body 5. In addition, the main component of the above terminal electrodes is contained, whereby the piezoelectric/electrostrictive membrane sensor 20 constitutes the piezoelectric/electrostrictive membrane sensor according to the present invention.

Figure 6:
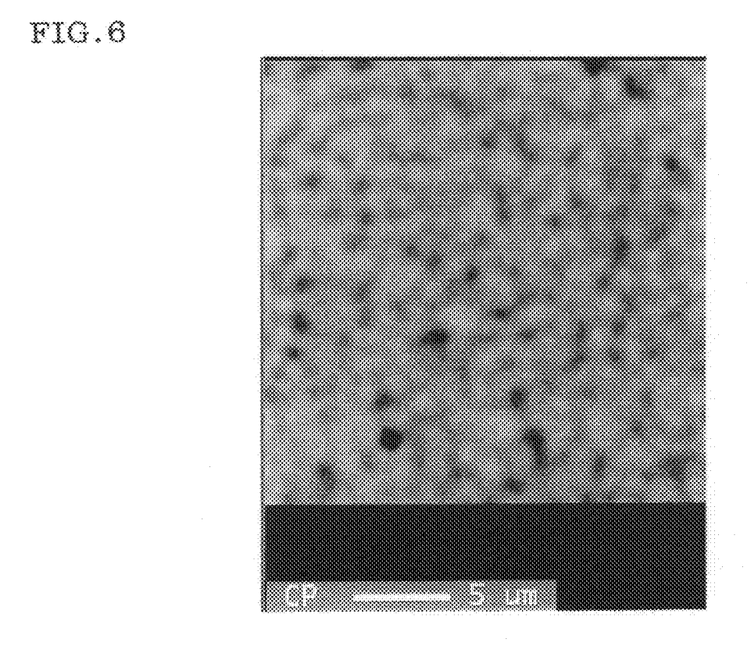
FIG. 6 is a diagram showing one embodiment of the piezoelectric/electrostrictive membrane sensor according to the present invention, and is a photograph showing the surface of a piezoelectric/electrostrictive body by the scanning electron microscope.
Figure 7:
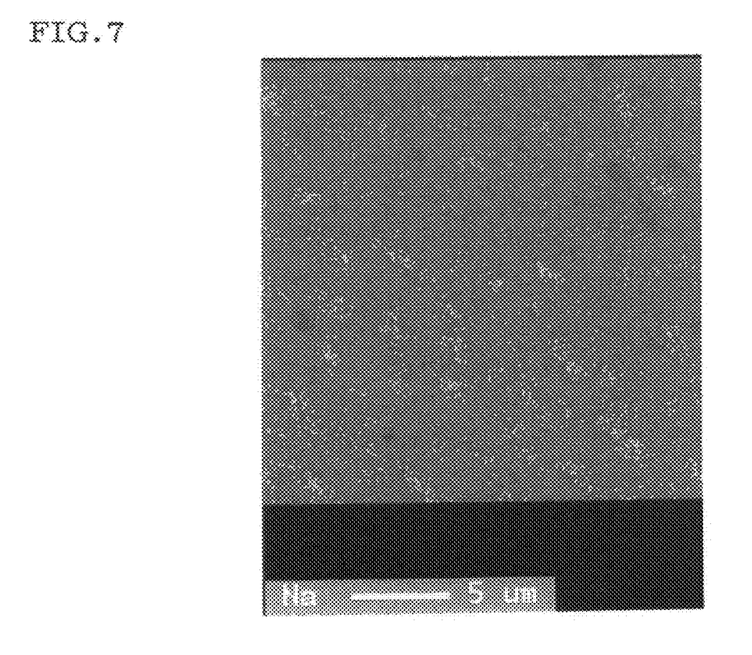
FIG. 7 is a diagram showing one embodiment of the piezoelectric/electrostrictive membrane sensor according to the present invention, and is a photograph showing the surface of the piezoelectric/electrostrictive body by the X-ray micro analyzer (EPMA, Electron Probe Micro Analyzer) and showing a behavior that sodium is present in the piezoelectric/electrostrictive body.
Figure 8:
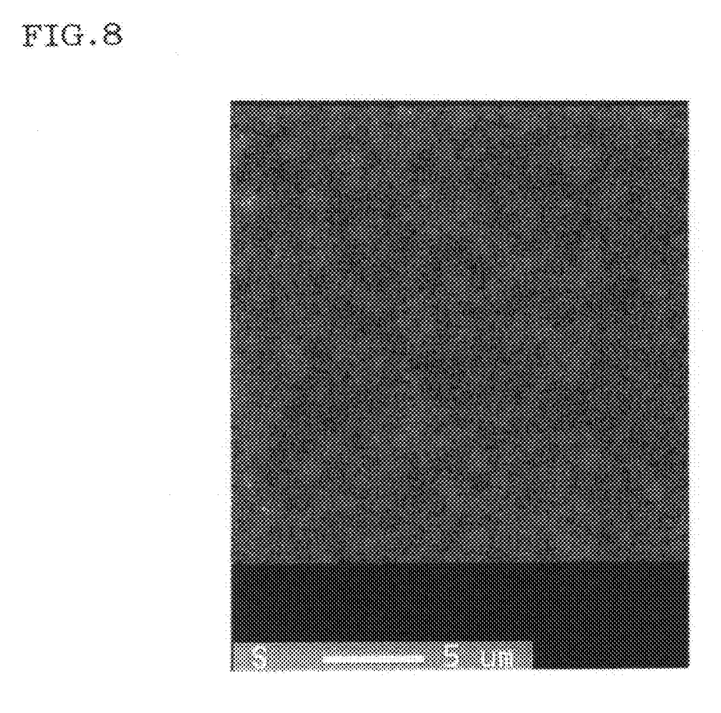
FIG. 8 is a diagram showing one embodiment of the piezoelectric/electrostrictive membrane sensor according to the present invention, and is a photograph showing the surface of the piezoelectric/electrostrictive body by the X-ray micro analyzer (EPMA, Electron Probe Micro Analyzer) and showing a behavior that sulfur is present in the piezoelectric/electrostrictive body.
Figure 9:
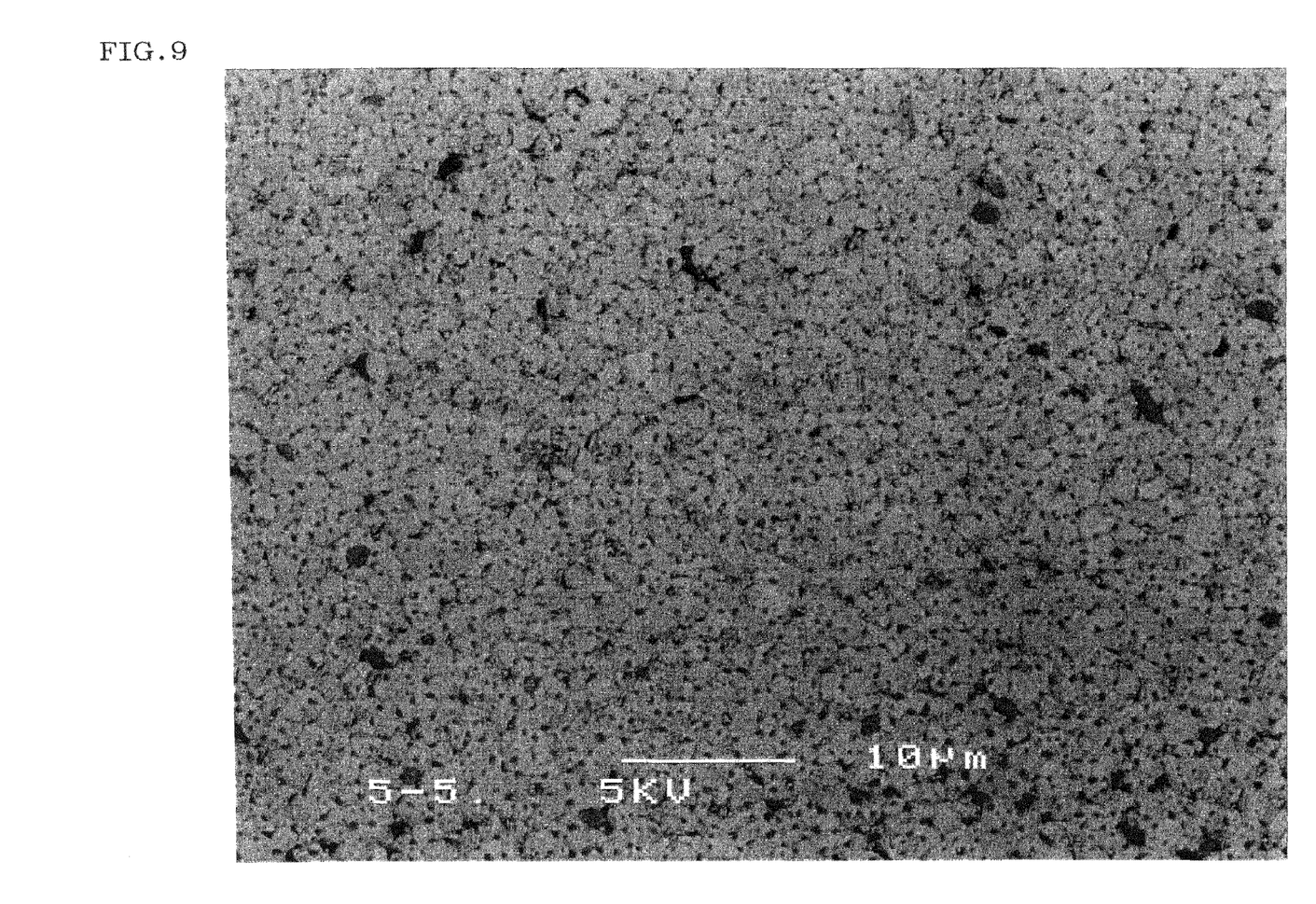
FIG. 9 is a diagram showing one embodiment of the piezoelectric/electrostrictive membrane sensor according to the present invention, and is a photograph showing the surface of a piezoelectric/electrostrictive body by the scanning electron microscope and showing a behavior that a compound of sodium and sulfur as a sulfide is contained in the piezoelectric/electrostrictive body.

FIGS. 6 to 9 are diagrams showing one embodiment of the piezoelectric/electrostrictive membrane sensor according to the present invention. FIG. 6 is a photograph showing the surface of the piezoelectric/electrostrictive body by a scanning electron microscope. FIGS. 7 and 8 are photographs showing the surface of the piezoelectric/electrostrictive body by the X-ray micro analyzer (EPMA, Electron Probe Micro Analyzer), in which FIG. 7 shows a behavior that sodium is present in the piezoelectric/electrostrictive body, and FIG. 8 shows a behavior that sulfur is present in the piezoelectric/electrostrictive body. It is to be noted that as described above the photograph of the EPMA shows that a target matter gradually increases (is present) in order of blue, green, yellow, vermillion and red (blue shows the smallest amount, and red shows the largest amount). Moreover, FIG. 9 is a photograph showing the surface of the piezoelectric/electrostrictive body by the scanning electron microscope and showing a behavior that the compound of sodium and sulfur as the sulfide is contained (is present) in the piezoelectric/electrostrictive body. In FIG. 9, portions appearing as black points are the compounds of sodium and sulfur. When the heat treatment (including the firing) is performed using a material containing the alkali metal or the alkaline earth metal as the material of the piezoelectric/electrostrictive body, as shown in FIGS. 6 to 9, the compound of sodium and sulfur as the sulfide can be contained near the surface of the piezoelectric/electrostrictive body 5.

It is to be noted that when the temperatures of the firing and the last heat treatment are adjusted or the content of the alkali metal or the alkaline earth metal contained in the material of the piezoelectric/electrostrictive body is adjusted, the amount of the sulfide (the compound of sodium and sulfur) contained near the surface of the piezoelectric/electrostrictive body 5 of the resultant piezoelectric/electrostrictive membrane sensor 20 can be adjusted. In the composition of the compound of sodium (Na) and sulfur (S), a molar ratio Na/S between sodium and sulfur is preferably in a range of 0.5 to 2. Moreover, as to the size and shape of the compound of sodium and sulfur, a shape projected from the surface is preferably a circular shape or an elliptic shape having a size of 100 to 500 nm. Furthermore, the compound of sodium and sulfur is present on the grain boundaries of piezoelectric particles or grains. When the compound is present on the grains, the compound is preferably present on not a ridge portion but a slope portion. According to these preferable embodiments, with a high humidity, the dielectric breakdown or the like is not generated, and characteristics can be satisfied.

(Step 14. Appearance Inspection) Finally, appearance is inspected, and then the sensors are shipped.

Next, the application of the piezoelectric/electrostrictive membrane sensor according to the present invention will be described. The piezoelectric/electrostrictive membrane sensor according to the present invention is usable as a sensor constituting a fluid characteristic measurement device. The fluid characteristic measurement device may be constituted of the piezoelectric/electrostrictive membrane sensor according to the present invention, a power source for applying a voltage across the upper electrode and the lower electrode to drive the piezoelectric/electrostrictive element of this piezoelectric/electrostrictive membrane sensor, and electric constant monitoring means for detecting the change of an electric constant accompanying the oscillation of the thin diaphragm portion of the piezoelectric/electrostrictive membrane sensor.

The fluid characteristic measurement device is a device capable of measuring the characteristics of a fluid by the detection of the electric constant by the electric constant monitoring means. In the fluid, when the piezoelectric/electrostrictive element is driven in the piezoelectric/electrostrictive membrane sensor to oscillate the thin diaphragm portion, the sensor receives a mechanical resistance by the viscosity resistance of the fluid, and the electric constant of the piezoelectric/electrostrictive element changes in a constant relation with respect to the mechanical resistance. Therefore, the change can be detected to measure the viscosity of the fluid.

In the basic principle of this fluid characteristic measurement device in measuring the characteristics of the fluid, there is used correlation between the amplitudes of the piezoelectric/electrostrictive element and the thin diaphragm portion as vibrators and the characteristics of the fluid which comes in contact with the vibrators. In a case where the fluid has the characteristics of the viscosity resistance, when the fluid has a large viscosity resistance, the amplitudes of the vibrators decrease. When the viscosity resistance decreases, the amplitudes of the vibrators increase. Moreover, a oscillation configuration in a mechanical system, for example, the oscillation of the vibrator can be replaced with an equivalent circuit of an electric system. In this case, it may be supposed that the amplitude corresponds to current. Moreover, the oscillation state of the equivalent circuit indicates various electric constant changes near a resonance point. Among electric constants such as loss coefficient, phase, resistance, reactance, conductance, susceptance, inductance and capacitance, in the fluid characteristic measurement device, the loss coefficient or the phase having the maximum or minimum change point of the change near the resonance frequency of the equivalent circuit is preferably used as an index. The detection of the loss coefficient or the phase can more easily be performed as compared with the other electric constants.

Needless to say, even in a case where the fluid has characteristics other than the viscosity resistance (e.g., the pressure of the fluid (needless to say, the presence of the fluid)), when an element influencing the oscillation of the vibrator is present in the fluid having the characteristics to be measured, the characteristics may be associated with the changes of the oscillations of the piezoelectric/electrostrictive element and the thin diaphragm portion to measure the characteristics. When the fluid is a solution and the concentration of the solution changes to change viscosity and density, the oscillation configurations of the piezoelectric/electrostrictive element and the thin diaphragm portion in the solution change, so that the concentration of the solution can be measured. That is, the fluid characteristic measurement device according to the present invention can measure the viscosity, density and concentration of the solution.

The piezoelectric/electrostrictive membrane sensor according to the present invention can measure the characteristics of the fluid, which can be used in detecting the flow state of the fluid or judging whether or not the fluid is present. When, for example, any fluid as a measurement target is not present, the amplitude changes of the vibrators (the piezoelectric/electrostrictive element and the thin diaphragm portion) become remarkable, and the changes are easily detected. Specifically, the piezoelectric/electrostrictive membrane sensor according to the present invention includes the monitoring of the dripping state of a medical dripping device, and the sensor can preferably be used as a measuring instrument sensor for monitoring the feed or infusion state of any solution, that is, whether or not the solution flows (as planned) (for a conventional technology concerning the dripping, refer to Patent Documents 5 and 6).

In the dripping device including a bottle containing a drug solution, a tube, a drip chamber through which the dripping of the drug solution can visually be checked, and an injection needle, the piezoelectric/electrostrictive membrane sensor according to the present invention is attached to one of the bottle, the tube and the drip chamber (several positions, if necessary). The device further includes a control monitoring device in which information on the flow state of the fluid or the presence of the fluid (the change of the electric constant) detected in this manner is input to perform computation, display, communication and the like, so that a dripping management device can be constructed. The computation includes the predicting of a dripping end time based on a timer disposed in the control monitoring device, the detection of an abnormality with the elapse of predetermined time and the like. A display target includes data such as a flow rate, and a warning. The communication includes the outputting to a nurse station. This dripping management device can be applied to the medical dripping device to ease patients and decrease burdens on nurses.

INDUSTRIAL APPLICABILITY

A piezoelectric/electrostrictive membrane sensor according to the present invention can be used as a sensor for measuring the characteristics of a fluid. Specifically, the sensor can be used as a sensor for each measuring instrument of viscosity, density or concentration. In addition, the sensor can preferably be used as a sensor of a measuring instrument which includes the monitoring of the dripping state of a medical dripping device and which monitors the feed or infusion state of any solution.

The invention claimed is:

1. A piezoelectric/electrostrictive membrane sensor comprising:
   a ceramic substrate having a thin diaphragm portion and a thick portion integrally provided on the peripheral edge of the thin diaphragm portion, and including a cavity formed by the thin diaphragm portion and the thick portion so as to communicate with the outside;
   a piezoelectric/electrostrictive element having a laminate structure arranged on the outer surface of the thin diaphragm portion of the ceramic substrate and including a membranous piezoelectric/electrostrictive body, and a lower electrode and an upper electrode between which the piezoelectric/electrostrictive body is sandwiched; and
   terminal electrodes which connect the lower electrode and the upper electrode to a power source;
   wherein the thin diaphragm portion of the ceramic substrate oscillates in conjunction with then, driving of the piezoelectric/electrostrictive element;
   wherein at least one of the upper, lower and terminal electrodes contain sulfur; and
   wherein the piezoelectric/electrostrictive body contains an alkali metal or an alkaline earth metal, and wherein the piezoelectric/electrostrictive body also contains a sulfide and a main component of the terminal electrodes near a surface of the piezoelectric/electrostrictive body.

2. The piezoelectric/electrostrictive membrane sensor according to claim 1, wherein the sulfide contained in the piezoelectric/electrostrictive body near the exposed surface of the piezoelectric/electrostrictive body is formed when the alkali metal or the alkaline earth metal contained in the piezoelectric/electrostrictive body bonds with the sulfur contained in the at least one electrode by a heat treatment.

3. The piezoelectric/electrostrictive membrane sensor according to claim 1, wherein the main component of the terminal electrodes contained near the surface of the piezoelectric/electrostrictive body is diffused from the terminal electrodes to the vicinity of the exposed surface of the piezoelectric/electrostrictive body by a heat treatment after terminal electrodes are formed.

4. The piezoelectric/electrostrictive membrane sensor according to claim 3, wherein the terminal electrodes are constituted of silver or a conductive material containing silver as a main component.

5. The piezoelectric/electrostrictive membrane sensor according to claim 1, wherein the terminal electrodes are constituted of silver or a conductive material containing silver as a main component.

6. The piezoelectric/electrostrictive membrane sensor according to claim 1, wherein the upper electrode is constituted of gold or a conductive material containing gold as a main component.

7. The piezoelectric/electrostrictive membrane sensor according to claim 1, wherein the lower electrode is constituted of platinum or a conductive material containing platinum as a main component.

8. The piezoelectric/electrostrictive membrane sensor according to claim 1, wherein the piezoelectric/electrostrictive body is constituted of $(Bi_{0.5}Na_{0.5})TiO_3$ or a piezoelectric/electrostrictive material containing this material as a main component.

* * * * *

UNITED STATES PATENT AND TRADEMARK OFFICE
CERTIFICATE OF CORRECTION

PATENT NO. : 7,714,480 B2
APPLICATION NO. : 12/316745
DATED : May 11, 2010
INVENTOR(S) : Takao Ohnishi, Hideki Shimizu and Takaaki Koizumi It is certified that error appears in the above-identified patent and that said Letters Patent is hereby corrected as shown below:

Column 7
  *Line 67*: please add -- ; -- after "portion"

Column 8
  *Line 8*: please replace the first occurrence of ";" with -- : --
  *Line 10*: please replace the first occurrence of ";" with -- : --
  *Line 11*: please replace the first occurrence of ";" with -- : --

Column 16
  *Line 36*, claim 1: please replace "then" with -- a --
  *Line 57*, claim 3: please add -- the -- before "termi-"

Signed and Sealed this

Seventeenth Day of August, 2010

David J. Kappos
*Director of the United States Patent and Trademark Office*